United States Patent
Takuma (12) 
(10) Patent No.: US 6,679,901 B1
(45) Date of Patent: Jan. 20, 2004

(54) AIRWAY

(76) Inventor: Norikata Takuma, No.793,Higashimotomachi2 chome, Kokubunji City, Tokyo (JP)

( * ) Notice: Subject to any disclaimer, the term of this patent is extended or adjusted under 35 U.S.C. 154(b) by 243 days.

(21) Appl. No.: 09/645,066

(22) Filed: Aug. 24, 2000

(30) Foreign Application Priority Data

Feb. 24, 2000  (JP) ........................................ 2000-047561

(51) Int. Cl.$^7$ ............................................. A61M 29/00
(52) U.S. Cl. ..................................... 606/196; 606/191
(58) Field of Search ................................ 606/196, 199, 606/204.45, 191, 119, 120, 197, 198; 128/207.18, 207.14; 600/184, 237

(56) References Cited

U.S. PATENT DOCUMENTS

| | | | | |
|---|---|---|---|---|
| 3,930,507 A | * | 1/1976 | Berman | 128/207.14 |
| 4,054,135 A | * | 10/1977 | Berman | 128/207.14 |
| 4,256,099 A | * | 3/1981 | Dryden | 128/200.26 |
| 4,356,821 A | * | 11/1982 | Rind | 128/207.14 |
| 4,363,320 A | * | 12/1982 | Kossove | 128/200.26 |
| 4,365,625 A | * | 12/1982 | Rind | 128/207.14 |
| D280,021 S | * | 8/1985 | Rind | D24/110 |
| 4,553,540 A | * | 11/1985 | Straith | 128/200.26 |
| 4,567,882 A | * | 2/1986 | Heller | 128/200.26 |
| 5,024,218 A | * | 6/1991 | Ovassapian et al. | 128/207.14 |
| 5,632,271 A | * | 5/1997 | Brain | 128/207.14 |

* cited by examiner

*Primary Examiner*—Michael J. Milano
*Assistant Examiner*—Jessica R. Baxter
(74) *Attorney, Agent, or Firm*—Dilworth & Barrese LLP.

(57) ABSTRACT

A medical airway instrument (1) is provided which is capable of facilitating creation of an air passage in the larynx to prevent collapse of the root of a patient's tongue, and having a lingual strip (2) curved in a longitudinal direction to conform with curvature of the tongue and palatal strip (3) curved in roughly the same manner as the lingual strip (2) such that the palatal and lingual strips (2,3) overlap in the anterior direction of curvature. The lingual and palatal strips (2,3) are rotatably coupled by a spindle (5) in the vicinity of a posterior part (2b, 3b) thereof. A stopper (4) is provided on a side of the lingual strip (2) to project in the direction of overlapping, in a position forward of the spindle (5) to hold anterior parts (2a, 3a) of the lingual and palatal strips (2,3) apart from one another at any desired gap without contact therebetween, to thereby secure a breathing passage (10) between the strips (2,3).

11 Claims, 8 Drawing Sheets

FIG. 7 (iii)

FIG. 8 (iii) (PRIOR ART)

AIRWAY

BACKGROUND OF THE INVENTION

1. Field of the Invention

The present invention relates to a medical instrument used in the medical field for assisting the patient's breathing, and more particularly, to a modification of a medical instrument called airway which improves the subsidence of the root of the patient's tongue to procure an air passage in the larynx.

2. Description of the Related Art

Figure 8:
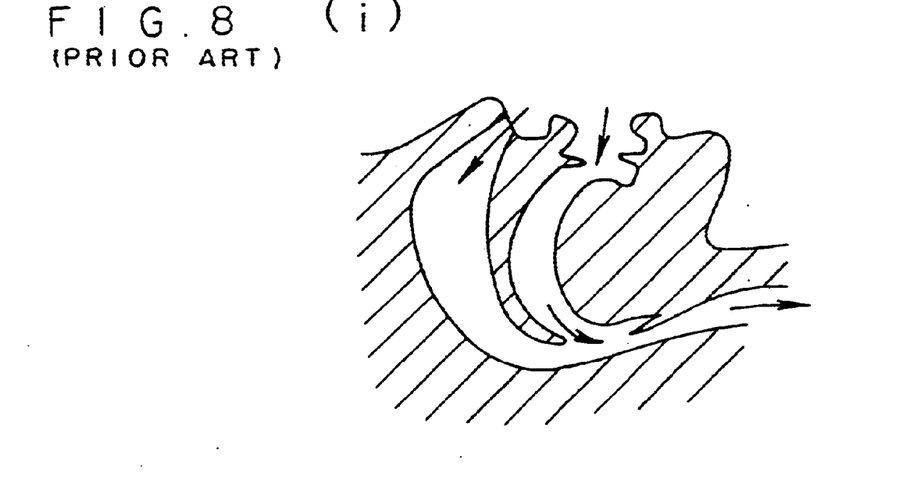

In a normal person, an air passage is secured in the larynx even when a person sleeps on the back so that air can flow through the rear of the root of the tongue to permit breathing without difficulty (See FIG. 8(i)). In a person with consciousness disorder, however, muscular tonus will disappear so that while sleeping in the supine position the root of the tongue will subside and thereby obstruct the passage of air, that is, the laryngeal airway with the result of causing breathing difficulty (See FIG. 8(ii)). This will inevitably result in a deterioration of the pathological condition.

Figure 7:
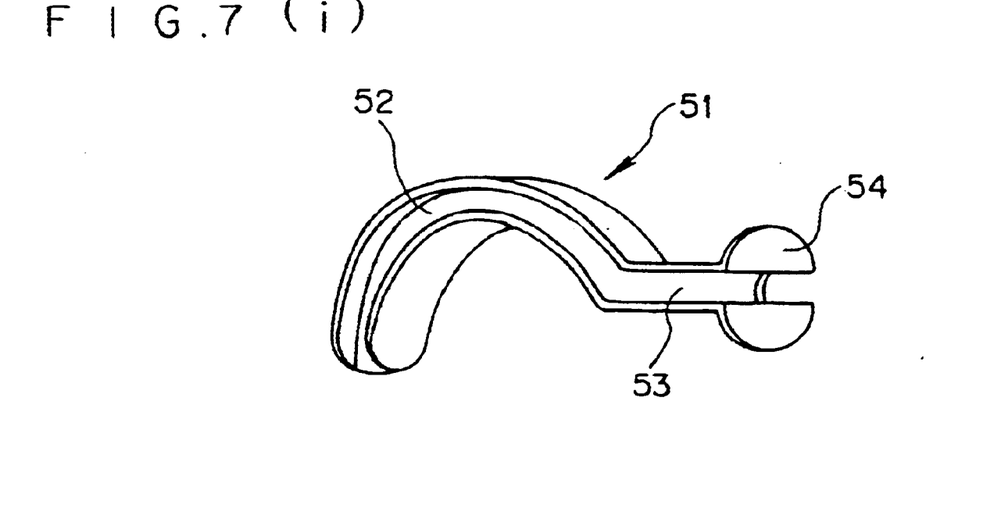

In such a case it is necessary to provide the necessary air passage for breathing (that is, to secure an airway) by some means or other to permit undisturbed breathing. The device that is extensive used in such cases consists, as shown in FIG. 7, of an umbrella-shaped retainer (54) which is used for operating the device and which protrudes from the mouth, a straight air-conducting part (53) which leads from said umbrella-shaped retainer to the interior of the oral cavity, and a curved intra-oral insert (52) which is continuous with said straight air-conducting part (53). With a section generally shaped in the form of Roman I, it uses recess cavities (55, 55) to provide spaces for breathing on both sides. In other words, it is a medical instrument (51) called an "airway." Said instrument (51) is inserted from the month into the larynx to lift up the root of the tongue (A) and thereby secure an air passage (See FIG. 8 (iii)).

Since the aforesaid medical instrument is not necessarily adapted to the shape of the tongue its use will, in certain cases, result in an unnatural condition. In other words, while, under some conditions, tongue which is a bundle of muscles may change its shape it will, in general, describe a natural curve and not assume an unnatural undular pattern. The aforesaid medical instrument, however, is bent at a steep angle after its transition of the extra-oral part to the intra-oral part in the portion leading from the straight air-conducting section to the curved intra-oral insert. As the aforesaid curved intra-oral insert is curved at a steep angle its bet and curved parts tend to apply pressure to the tongue in the direction of the root of the tongue.

Moreover, the aforesaid medical instrument is difficult to insert into the laryngeal region. In other words, said instrument has a particular fixed shape as has been explained herein above. When it is inserted, its bent and curved parts will therefore hit against various parts of the mouth such as, for example, the lips, incisors, the tongue or the palate, and thus be extremely difficult to handle.

Furthermore, the aforesaid medical instruments present difficulty in the withdrawal of sputum. In other words, the insertion of a suction tube can take place from either side of the recessed parts provided on both sides of said instrument with a section generally shaped in the form of a Roman I. However, since said instrument has a particular fixed shape as explained herein above, the suction tube will impinge on its bent and curved parts and will thus be incapable of being inserted farther to the back of the throat.

Furthermore, the aforesaid medical instrument is not capable of lifting up the root of the tongue to an adequate extent. In other words, since the object of this type of instrument is to secure an air passage by inserting the previously described instrument having a particular fixed shape between the tongue and the palate, the space provided as an air passage will be determined by the cross-sectional size of said instrument. When, for this purpose, the section of said instrument is made large in a deliberate attempt to ensure that the root of the tongue is lifted up to an adequate extent, a new problem will arise in that it will be difficult to insert the aforesaid instrument because of its particular fixed shape.

Moreover, the aforesaid medical instrument is difficult to clean after use. In other words, in view of the problems associated with the cleaning and disinfecting of the medical instrument in terms of the growth of bacteria the effectiveness of the disinfectant will be substantially impaired in the presence of residual protein matter residing on the surface of the instrument and bacterial growth will be facilitated. The aforesaid instrument, however, has a number of recess cavities that are difficult to clean because of its Roman I shaped section as explained herein above.

SUMMARY OF THE INVENTION

In order to resolve these difficulties, the inventor has, as a result of intensive investigation, created an arrangement of two strips curved as a gentle angle in the lengthwise direction in order to facilitate insertion into the laryngeal area and suited to the curvature of the tongue in such a manner as to provide a space passing between the strips in the lengthwise direction by positioning the strips separately from each other. Furthermore, the aforesaid two long and narrow strips are arranged in such a manner that the extent of separation of their anterior parts (on the side of the root of the tongue) can be adjusted by providing a spindle to couple the two strips in a freely movable manner.

BRIEF DESCRIPTION OF THE DRAWINGS

FIG. 1 is an oblique view of the Airway in accordance with the present invention showing the holding position at the smallest gap (i) and in a holding position at an increased gap (ii).

FIG. 4 is a lateral section outline view showing the Airway in accordance with the present invention in the inserted position in the laryngeal region (i) and a lateral section outline view showing it in the extended position after insertion (ii).

FIG. 7 is an oblique view (i), a lateral view (ii) and lateral vertical section outline view (iii) showing the Airway in accordance with the prior art.

FIG. 8 is a lateral section view showing the condition of the respiratory tract during sleep in the supine position (i), a lateral section outline view showing a condition in which the air passage is blocked during sleep in the supine position (ii), and a lateral section outline view showing the conventional Airway inserted into the laryngeal region.

Furthermore, as employed in the drawings the symbol A refers to the root of the tongue, 1 to the Airway, 2 to the long and narrow strip (lingual strip), 2a to the anterior part thereof, 2b to the posterior part thereof, 3 to the long and narrow palatal strip, 3a, to the anterior part thereof, 3b to the posterior part thereof, 4 to the stopper, 5 to the spindle, 6 to the spindle bearing, 7 to the omitted round groove, 7' to the notched part, 8 to the rotating leg, 9 to the round projection, 10 to the breathing space, 11 to the Airway of a different embodiment of the invention, 12 to the long and narrow lingual strip, 13 to the corresponding palatal strip, 15 to the insert passage for the medical instrument, 21 to the Airway of yet another embodiment of the invention, 22 to the lingual strip thereof, 23 to the palatal strip thereof, 25a and 25b to the optic fibers, 26 to the connector, 51 to the conventional medical instrument (Airway), 52 to the curved intra-oral insert, 53 to the straight air-conducting part, 54 to the umbrella-shaped retainer and 55 to the recess cavities.

DESCRIPTION OF THE PREFERRED EMBODIMENTS

The present invention relates to an instrument consisting of a long and narrow lingual strip curved in the longitudinal direction in such a manner as to conform to the curvature of the tongue and a long and narrow palatal strip curved in roughly the same manner as said lingual strip, with said lingual and said palatal strips arranged in such a manner as to overlap in the direction of their curvature, and coupled in such as manner as to be freely movable by providing a spindle in the proximity of the posterior parts of said strips, and shaped, furthermore, in such a manner that the anterior parts of both strips can be maintained at any gap aperture without contacting each other by providing, at least in one direction, a stopper projecting from said spindle in the overlap direction toward the anterior part. As the two-strip unit consisting of the lingual strip and the palatal strip, respectively, is arranged in such a manner as to overlap while maintained separate over the entire length from the anterior to the posterior part it is therefore possible to secure a breathing space between them in the longitudinal direction and a passage for inserting a medical instrument such as a suction tube. Since, furthermore, the two strips are coupled in such a manner as to be freely movable by providing a spindle it is possible to adjust to gap at the anterior end (on the side of the root of the tongue) to any desired aperture by holding the aforesaid two strips in the vicinity of their posterior parts as required, in other words, it is possible to adjust the amount of lift of the root of the tongue and insert the aforesaid medical instrument without difficulty by mutually opening said anterior parts in such a manner as to increase the curvature.

Furthermore, the present invention relates to an instrument in which a stopper and spindle are provided on the lateral part of the lingual strip and/or the palatal strip. In other words, the essential function required from the Airway is to permit the passage of air and it is therefore desirable to secure a large space for this purpose in the center of the Airway in the longitudinal direction by separately arranging stoppers and spindles on either side. As a result, the center will no longer be obstructed by the structural parts of the instrument as has been the case with the conventional medical instrument (airway) and a shape conforming to the previously described essential function required from an Airway is achieved, in other words, a shape ensuring a large space for the passage of air in the center. As a result, this also facilitates the withdrawal of sputum and the insertion of other medical instruments such as a suction tube and furthermore, permit direct visual observation of the pharynx which had not been possible with the conventional type of medical instrument.

Moreover, the present invention relates to an instrument in which a rotating spindle coupling the lingual and palatal strips is provided in a position in which it makes contact with the incisors when inserted into the oral cavity. In other words, the two movably coupled strips (lingual and palatal strips) are arranged so that the root of the tongue can be lifted by opening the anterior parts (root of tongue) with the spindle in the middle. When said spindle is positioned farther inward (toward the anterior parts) with respect to the position in which it makes contact with the incisors it will be difficult for the anterior ends to open as the patient uses force and bites his teeth to close his mouth; and when, on the other hand, said spindle is positioned farther outward (toward the posterior parts) with respect to the position in which it makes contact with the incisors that are an intermediate position the incisors will thus make contact with the coupling spindle that forms the axis of rotation even when the patients closes his mouth with force so that it can be easily handled without having any effect on the opening and closing action of the anterior end of the Airway and it is possible to lift the root of the tongue without difficulty.

Furthermore, the present invention relates to an instrument designed in such a manner that it forms a large curvature in the direction in which the lingual and/or palatal strips are separated from each other. In other words, when the lingual strip and the palatal strip which are curved in this manner are arranged so that they will overlap towards the direction of curvature a space for the passage of air provided in the center will be secured but this space will be covered up by the posterior part of the palatal strip so that it will be difficult to visually observe the pharynx directly. Furthermore, when, in certain cases, the aperture of the anterior parts (on the side of the root of the tongue) is opened to a large extent the danger does exist that when the posterior parts are gripped somewhat too firmly the posterior ends of the lingual and palatal strips will mutually come together and obstruct said air passage space. It is, consequently, desirable that the posterior ends of the lingual and palatal strips should be curved in the direction in which the move apart from each other. By this means, the air passage space provided in the center will not be obstructed by the posterior ends of the palatal strip even when arranged in such a manner that the lingual and palatal strips will overlap since the posterior end of the palatal strip is curved in the direction in which it interacts with the posterior end of the lingual strip so that it will be possible to visually observe the pharynx directly. When furthermore, the aperture of the anterior ends (on the side of the root of the tongue) is opened to a large extent, there will consequently be no danger that the aforesaid air passage space might be closed since the posterior ends of the lingual and palatal strips will not easily come together even if, for example, the posterior ends are gripped with a somewhat excessive force. Moreover, as a result of providing a curvature in the direction of mutual separation, it will also be possible to eliminate the danger that the widely opened posterior end might move as a retainer and the Airway itself fall unintentionally into the mouth.

Furthermore, the present invention also relates to an instrument in which perforated insert passages for the insertion of medical instruments are provided in the longitudinal direction in the interior or on the surface of the lingual strip. In other words, with the present invention described herein above it is possible to facilitate the insertion medical instruments such a suction tubes for the extraction of sputum since the air passage space is shaped in such a manner as to ensure a large space in the center. Furthermore, by providing insert passages for the insertion of medical instruments are provided in the longitudinal direction in the interior or on the surface of the lingual strip, it is possible to facilitate the insertion of said medical instruments still further in that the medical instruments such as suction tubes and/or optic fibers are bent without misalignment with respect to the shape of the aforesaid lingual strip and can thus be inserted deep into the interior without difficulty.

Furthermore, the present invention also relates to an instrument designed in such a manner that optic fibers are embedded in the longitudinal direction in the interior of the lingual strip or that the lingual strip consists of a transparent material. In other words, in the present invention described herein above it is possible to visually observe the pharynx directly since a large air passage space is secured in the center. However, since the pharyngeal region lies far back it is difficult to observe it visually without adequate brightness. In order to permit the projection of bright illumination on the pharynx it is desirable therefore to embed optic fibers in the longitudinal direction in the interior of the lingual strip or make the lingual strip itself from a transparent material. By this means, it is possible to create the desirable environmental for the observation of the pharyngeal region by connecting the intra-orally optic fibers (that is, the optic fibers embedded in the interior of the lingual strip) with other optic fibers that are extra-orally provided in the case of optic fibers being embedded in the interior of the lingual strip or by brightly illuminating the pharyngeal region by letting the light of an extra-oral light source pass through the lingual strip and be refracted in the lingual strip in the event that the lingual strip itself consists of a transparent material.

Furthermore, the present invention also relates to an instrument in which the lingual and palatal strips are detachably coupled. For, it is desirable that said instrument should be shaped without or with the least possible recesses for greater ease of cleaning since the presence of residual protein matter on the surface of the medical instrument will substantially impair the effect of disinfectants and facilitate bacterial growth. Yet, even without any recesses in the shape of said instrument itself, it will be equally as difficult to clean the spindle as it would be to clean recesses when there is a spindle coupling the lingual and palatal strips in a freely movable manner. The best way to facilitate the cleaning of said spindle may be to couple the lingual and palatal strips in a detachable manner. By this means, the detached lingual and palatal strips can be adequately cleaned by brushing from all directions as there are no recesses making the cleaning difficult and as there is no similar hollow parts such as a spindle either.

The following descriptions explain an embodiment of the present invention.

Figure 1:
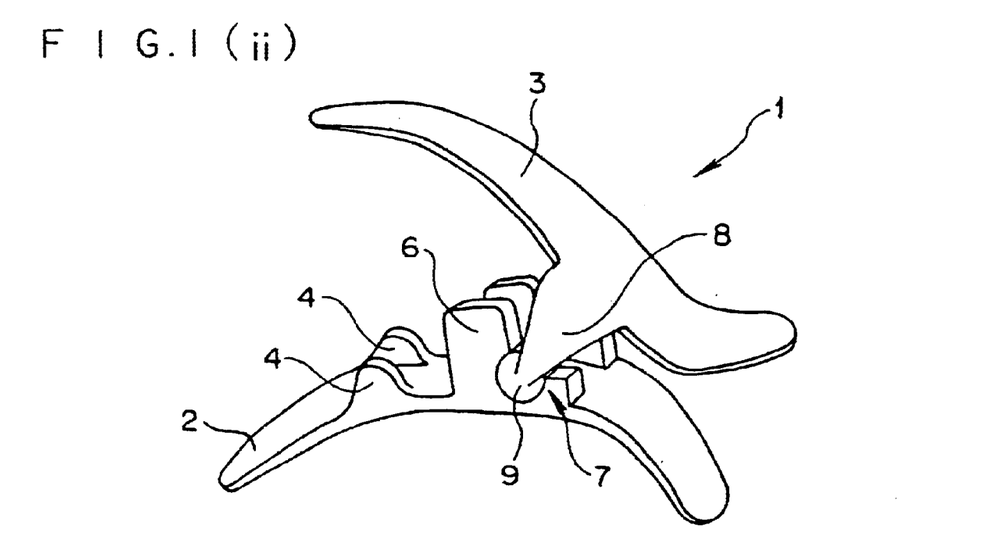
Figure 1I:
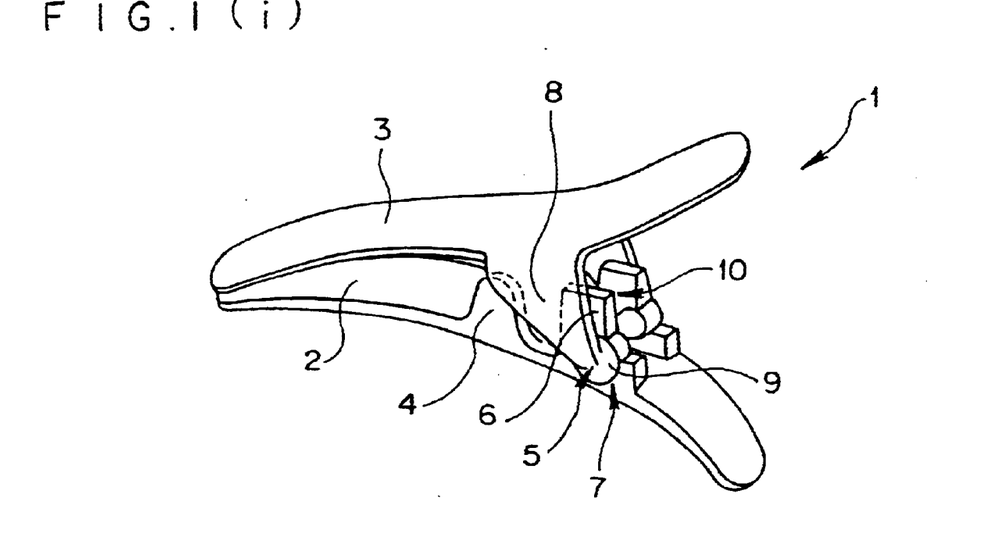
Figure 2:
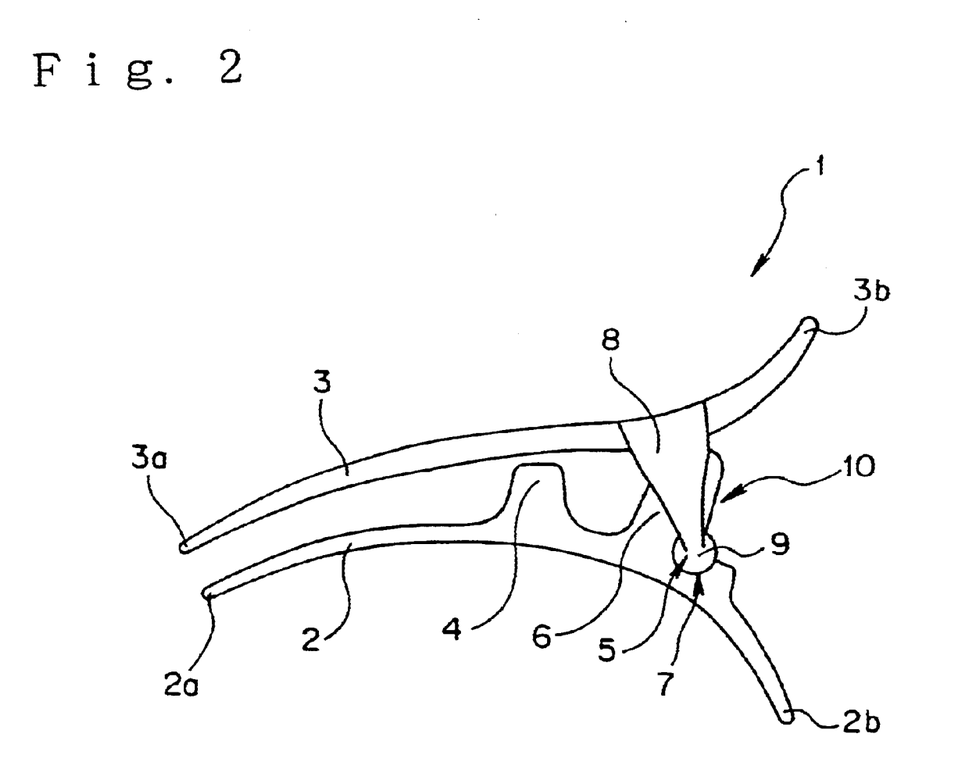
FIG. 2 is a side view of the Airway in accordance with the present invention showing the holding position at the smallest gap.

The Airway (1) according to the present invention consists of a hard synthetic resin in its entirety, and as shown in FIGS. 1 and 2, the lingual strip (2) which is curved in the longitudinal direction in such as manner as to conform to the curvature of the tongue and the palatal strip (3) curved in roughly the same manner as said lingual strip (2) are arranged in such a manner as to overlap in the direction of the curvature, and rotatably coupled by providing a spindle (5) in the vicinity of the posterior part thereof and, furthermore, a stopper (4) projecting in the direction of overlap is provided on the side of the lingual strip (2) in a position forward of said spindle (5) to hold the anterior parts of the lingual strip (2) and of the palatal strip (3) at any desired gap without making contact thereby securing a breathing space (10) between the strips. Moreover, even when said stopper (4) is arranged in such a manner as to project in the direction of overlap on the side of the palatal strip (3) there will be no problem whatever since this is functionally identical. However, when a medical instrument such as a section tube is inserted in the breathing space (10) it will serve as a guide to prevent said medical instrument from sliding to the side so that it is desirable to install it on the lingual strip (2) as described herein above.

Provided on the lingual strip (2) is a spindle bearing (6) with an omitted round groove (7) recessed in a part near the posterior end (2b) of said lingual strip (2) in such a manner as to extend in the upward direction warped in a convex-shaped curvature in the longitudinal direction so as to conform with the curvature of the tongue, in other words, in the direction of the palatal strip (3) which is arranged in an overlapping manner. Further, in the vicinity of the anterior part thereof (2a), a stopper (4) protruding in the direction of overlap of the palatal strip (3), in other words, in the direction towards the previously described curvature is provided. Moreover, said spindle bearing (6) and said stopper (4) are both separately and individually provided on either side of the lingual strip (2).

In contrast, the palatal strip (3) is provided in the vicinity of its posterior end (3b) with a rotating leg (8) in such a manner as to extend downward in a convex-shape curvature in the longitudinal direction, in other words, in the direction of the lingual strip (2) arranged in an overlapping manner. Furthermore, at the anterior end of said rotating leg (8) a round protrusion (9) fitting into the omitted round groove (7) of the spindle bearing (6) in said lingual strip (2), with said round protrusion (9) fitting in said omitted round groove (7) and thereby being rotatably supported. Moreover, said rotating leg (8) and the round protrusion (9) at the anterior end thereof are both installed individually and separately on either side of the palatal strip (3). In this manner, the lingual strip (2) and the palatal strip (3) as well as such parts as the stopper (4) are finished in a beveled or rounded shape so as to prevent them from causing bruising in the oral cavity and to facilitate cleaning.

Further, the freely rotating spindle (5) mutually coupling the lingual strip (2) and palatal strip (3) is placed in such a position as to adjoin the incisors when inserted into the mouth, and the anterior parts (2a, 2b) of the Airway (1) can be easily operated to open and close without affecting in any way whatever the manner in which the patient bites his teeth together.

Furthermore, the posterior parts (2b, 3b) of the lingual strip (2) and of the palatal strip (3) are formed in such a manner as to facilitate the operation of separating the anterior ends by mutually holding them and also to provisionally secure on the lips and bend at a large curvature in the direction toward mutual separation.

Further, the lingual strip (2) and the palatal strip (3) are mutually coupled in that the round protrusion (9) provided in the anterior part of the rotating leg (8) engaged is, and is supported by, the spindle bearing (6) which has a omitted partially notched round groove (7) as described herein above, whereby the inner surface of the omitted round groove (7) in said spindle bearing (6) and the outer surface of the round protrusion (9) on said rotating leg (8) are mate and form a snug fit so that there is no backlash movement and the rotating mechanisms are smoothly compatible.

Figure 3:
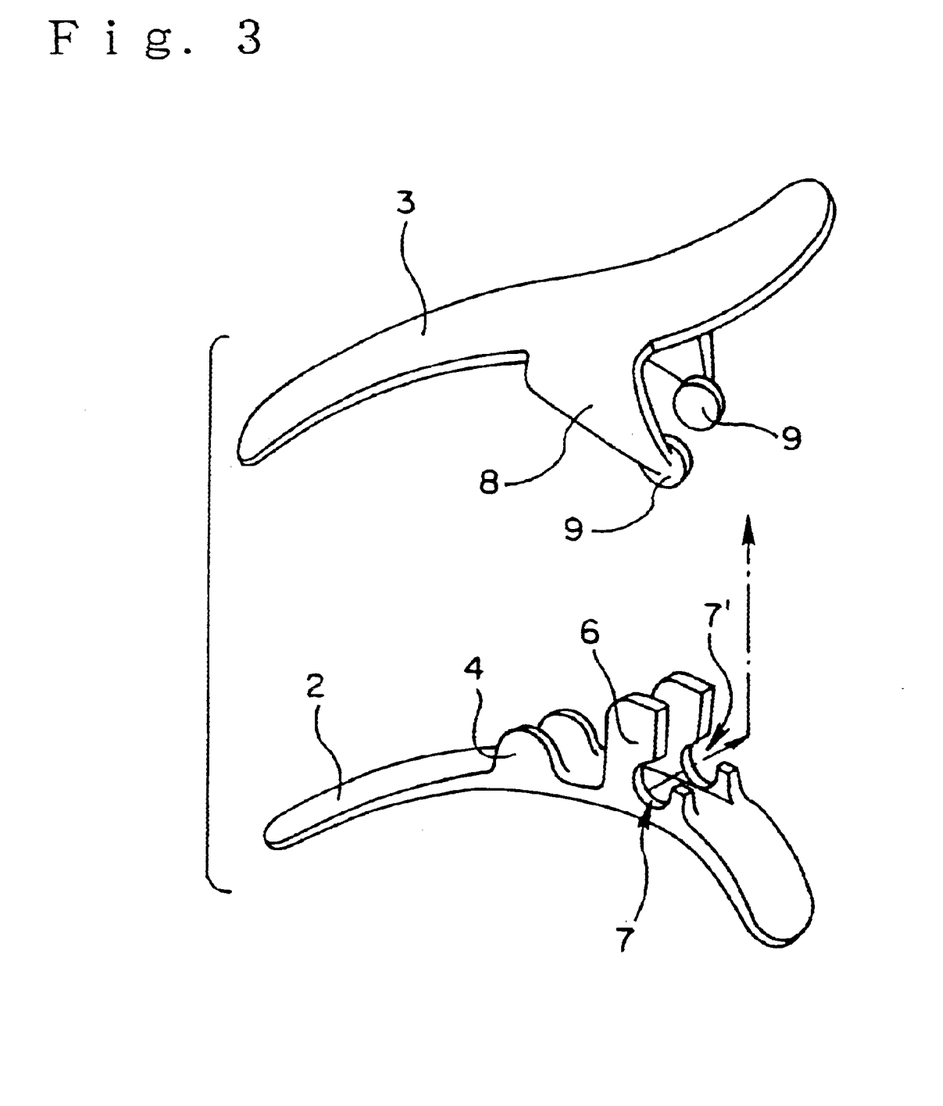
FIG. 3 is an oblique view showing the Airway in accordance with the present invention in the detached condition.

The notch (7') in the omitted round groove (7) provided in the spindle bearing (6) is caused to slide in the horizontal direction by adjusting said rotating leg (8) with said notch (7'). As a result, it is possible to separate the lingual strip (2) and the palatal strip (3) from each other (See FIG. 3).

Figure 4:
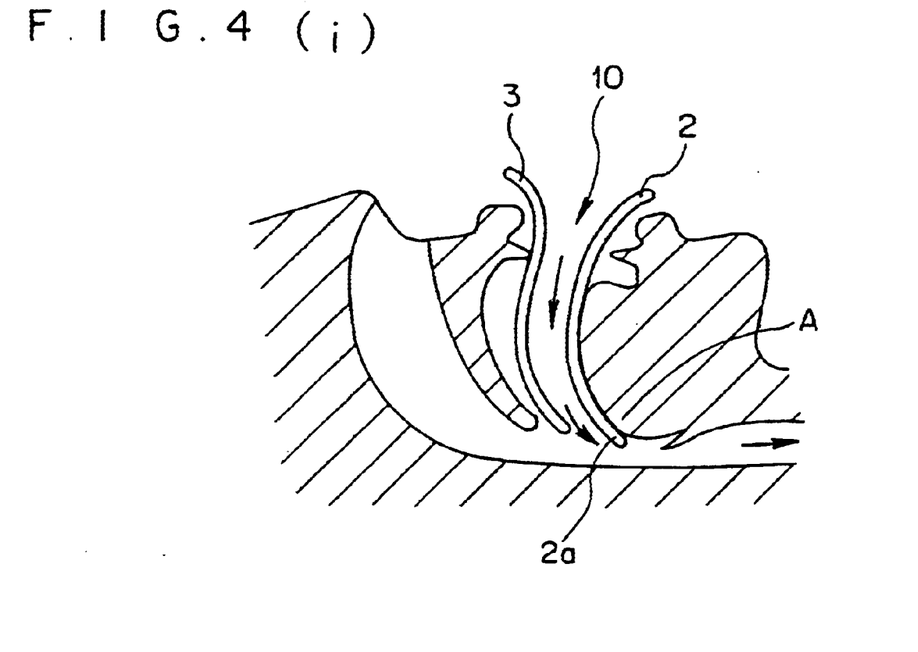

The Airway (1) constructed in this manner is capable, as shown in FIG. 4 of securing a space (10) between the lingual strip (2) and said palatal strip (3) on insertion into the larynx from the oral cavity and of securing an air passage to avoid breathing disorder due to a collapse of the root of the tongue by the anterior part (2a) of said lingual strip (2) lifting the root of the tongue (A). (See FIG. 4 (i). Further, by holding both posterior parts (2b, 3b) of the lingual strip (2) and of the palatal strip (3), respectively, when necessary, it is possible to widen the gap aperture in the anterior end (on the side of the root of the tongue) and adjust it to any desired aperture to increase the curvature and thereby improve the lift of the root of the tongue (A) and facilitate the insertion of medical instruments such as a suction tube.

Figure 5:
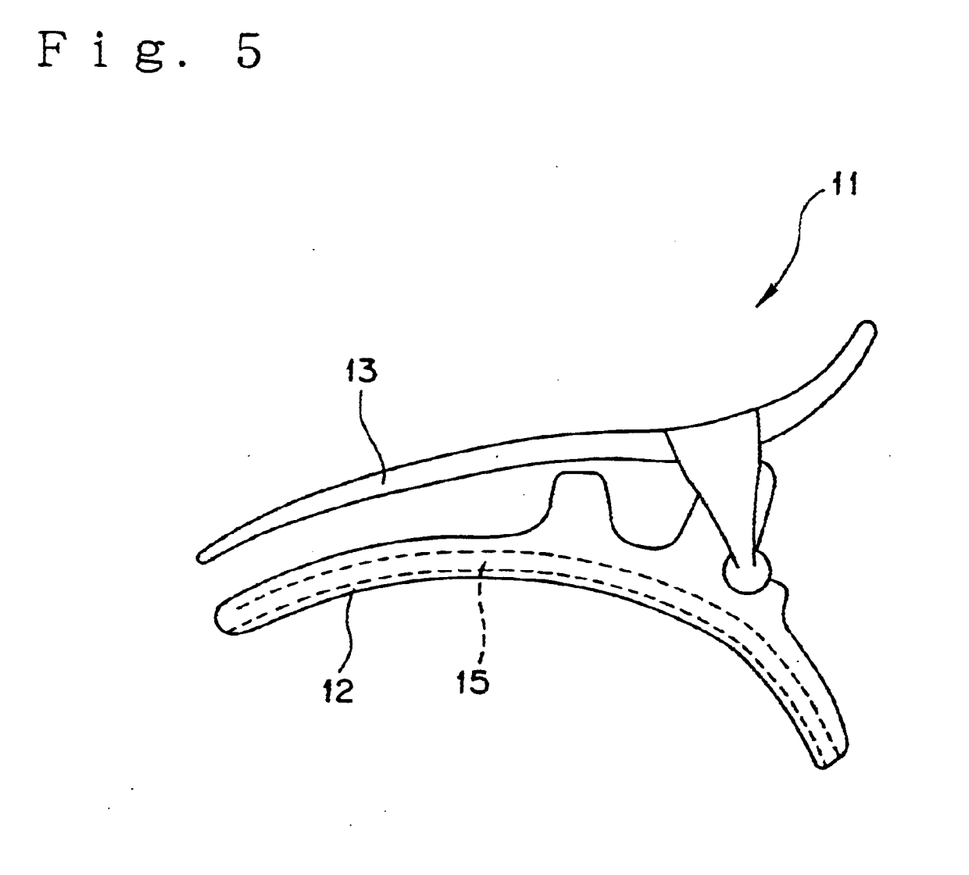
FIG. 5 is a side view showing a different embodiment of the Airway in accordance with the present invention.

Moreover, as shown in FIG. 5, the present invention may also relate to an airway (11) capable of providing greater ease in inserting medical instruments such as a suction tube and optic fiber by provide insertion passages (holes) (15) drilled in the longitudinal direction in the interior of the lingual strip (12) or on the surface thereof.

Figure 6:
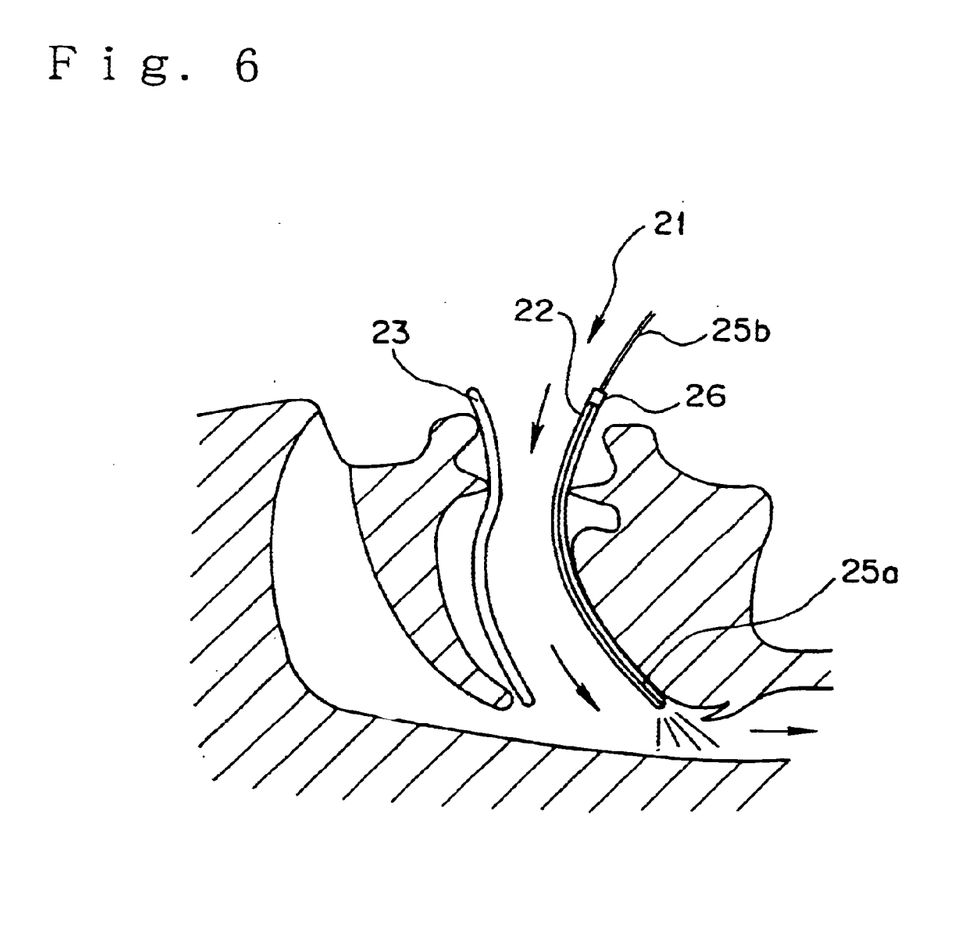
FIG. 6 is a lateral outline view showing a different embodiment of the Airway in accordance with the present invention in the inserted position in the laryngeal region.

Furthermore, as shown in FIG. 6, the present invention may also relate to an airway (21) capable of creating a favorable environment for the observation of the pharynx by using the light of an extra-oral light source to illuminate the pharynx from the anterior end by embedding optic fibers (25a) in the longitudinal direction in the interior of the lingual strip (22) or by connection with other optic fibers (25b) provided extra-orally with a connector (26), or, although not shown in the figures, the present invention may relate to an airway capable of creating a favorable environment for the observation of the pharynx by shining light on the pharynx at the same level of brightness, by using a transparent material for the lingual strip, by causing the light from an extra-oral light source to pass through, or be refracted in, said lingual strip.

By this means, since the two strips consisting of the lingual strip and the palatal strip, respectively, are arranged, in accordance with the present invention in such a manner as to overlap while being separated over their entire length by the stopper, it is possible to obtain a breathing space passing between them in the longitudinal direction and achieve a space for inserting medical instruments such as a suction tube. Moreover, by installing the stopper and the spindle coupling the lingual strip and the palatal strip on the sides of the lingual and/or palatal strips it is possible provide said breathing space and secure a passage for inserting medical instruments in the center in the longitudinal direction, whereby the suction operation for removing sputum and the insertion of other medical instruments such as suction tubes is facilitated and the pharynx can be visually observed directly which had not been possible with the conventional type of medical instrument.

Since, in accordance with the present invention, the lingual strip and the palatal strip are coupled via a spindle in a freely movable manner, it is possible to adjust the aperture (gap) of the anterior end (on the side to the root of the tongue) of said strips and thereby increase the lift of the root of the tongue and thus facilitate the insertion of medical instruments.

Since, furthermore, in accordance with the present invention the rotating spindle coupling the lingual and palatal strips are placed in such a position as to make contact with the incisors when the airway has been inserted, it is possible, by allowing the incisors to make contact with the coupling spindle acting as the axis of rotation, to achieve great ease of operation without any influence whatever on the closing and opening of the anterior end of the airway even when the patient closes his mouth with force, so that, as a result, it is possible to lift the root of the tongue effectively.

Since, furthermore, in accordance with the present invention the posterior parts of the lingual strip and/or the palatal strip are installed in such a manner that a large curvature is obtained in the direction in which the move apart from each other, there is no danger that the breathing space secured in the center will not be covered up by the posterior part of said palatal strip even when the lingual strip and the palatal strip are arranged in such as manner as to overlap, or that the posterior ends of the lingual strip and the palatal strip might easily come together even when, for example, the posterior ends are gripped with excessive force when increasing the aperture of the anterior ends (at the root of the tongue), wherefore it is possible to visually observe the pharynx directly with accuracy in any condition. Furthermore, by bending so that the posterior parts open (spread out), it is possible to exclude the danger that the airway itself might unintentionally fall into the mouth.

Furthermore, by providing, in accordance with the present invention, a perforated passage for inserting medical instruments in the longitudinal direction either in the interior of the lingual strip or on the outer surface thereof, it is possible easily to insert medical instruments such as suction tubes for withdrawing sputum without any positional displacement by bending them in accordance with the shape of the lingual strip, and thereby facilitate the insertion of said medical instruments to a greater extent.

Furthermore, by embedding optic fibers in the longitudinal direction in the interior of the lingual strip or by constructing the lingual strip from a transparent material, it is possible, in accordance with the present invention to create a more favorable environment for the observation of the pharynx by illuminating the pharynx with the bright light produced from an extra-oral light source.

Since, moreover, the lingual strip and the palatal strip are coupled in a detachable manner it is possible, in accordance with the present invention, to clean the airway properly by brushing from all directions seeing that once the two strips are separated from each other, there are no recessed parts that are difficult to clean such as a spindle.

What is claimed is:

1. An airway comprising a long and narrow lingual strip (2) curved in a longitudinal direction, and a long and narrow palatal strip (3) curved in roughly the same manner as said lingual strip (2), said lingual and palatal strips (2,3) arranged to overlap towards an anterior direction of curvature, a spindle (5) being arranged proximate to posterior parts (2b, 3b) of said strips (2,3) to couple the same together freely movably with respect to one another, said strips (2,3) shaped such that anterior parts thereof (2a, 3a) can be maintained at any gap there between without contacting each other, and a stopper (4) positioned upon at least one of said lingual and palatal strips (2,3) between said spindle (5) and the anterior parts (2a, 3a) in the overlapping direction, to maintain said anterior parts (2a, 3a) apart from on another at all times when said strips (2,3) are coupled together, additionally comprising a spindle bearing (6) situated on one of said strips (2,3) and having a mounting groove (7) therethrough, said spindle (5) comprising a rotating leg (8) projecting from the other strip (2,3) and having a protrusion (9) at an end thereof arranged to be rotatable received in said groove (7), and additionally comprising two spindle bearings (6), stoppers (4) and spindles (5) mounted upon lateral sides of said respective strips (2,3) to define a longitudinally extending air channel (10) therebetween when said strips (2,3) are rotatably coupled together.

2. The airway of claim 1, characterized in that the spindles coupling the lingual and palatal strips are placed in a position in which they make contact with the incisors when inserted in the oral cavity.

3. The airway of claim 1, wherein said posterior parts (2b, 3b) of at least one of said lingual strip (2) and palatal strip (3) are bent at a large curvature in the direction in which they separate from each other.

4. The airway of claim 1, characterized in that perforated passages for the insertion of medical instruments are provided on the lingual strip in the longitudinal direction.

5. The airway of claim 1, characterized in that optic fibers are embedded in the lingual strip in the longitudinal direction.

6. The airway of claim 1, characterized in that the lingual strip is made of a transparent material.

7. The airway of claim 1, characterized in that the lingual and palatal strips are detachably coupled.

8. The airway of claim 1, wherein when said strips (2,3) are rotatably coupled together at said spindles (5), said strips (2,3) are maintained apart from one another over the entire longitudinal length thereof between said anterior (2a, 3a) and posterior (3b,2b) parts to permit insertion of an instrument therebetween at all times.

9. The airway of claim 1, wherein said spindles (5) are mounted upon said palatal strip (3) and said spindle bearings (6) upon said lingual strip (2).

10. The airway of claim 9, wherein said stoppers (4) are mounted upon said lingual strip (2).

11. The airway of claim 1, wherein said strips (2,3) are structured and arranged to be securely coupled together by laterally sliding said strips (2,3) with respect to one another to securely mate said projections (9) within said respective grooves (7).

\* \* \* \* \*